United States Patent [19]

Laskowski

[11] Patent Number: 5,420,507
[45] Date of Patent: May 30, 1995

[54] METHOD AND APPARATUS FOR SENSING A TARGET CHARACTERISTIC BY MEASURING BOTH IMPEDANCE AND RESONANT FREQUENCY OF A TANK CIRCUIT

[75] Inventor: Edward L. Laskowski, 6154 Winchester Dr., Seven Hills, Ohio 44131

[73] Assignee: Edward L. Laskowski, Seven Hills, Ohio

[21] Appl. No.: 952,305

[22] Filed: Sep. 28, 1992

[51] Int. Cl.$^6$ ............... G01N 27/72; G01R 33/12; G01R 27/00
[52] U.S. Cl. ............... 324/236; 324/207.16; 324/230; 324/655
[58] Field of Search ............... 324/207.16, 207.26, 324/229, 230, 231, 236, 652, 655, 668, 675, 682

[56] References Cited

U.S. PATENT DOCUMENTS

| | | | |
|---|---|---|---|
| 3,600,676 | 8/1971 | Lugwig et al. | 324/668 |
| 3,732,503 | 5/1973 | Rapp et al. | |
| 3,796,295 | 3/1974 | Montolivo et al. | |
| 4,068,189 | 1/1978 | Wilson | |
| 4,151,904 | 5/1979 | Levasseur et al. | |
| 4,230,987 | 10/1980 | Mordwinkin | |
| 4,727,322 | 2/1988 | Lonchampt et al. | |
| 4,754,862 | 7/1988 | Rawicz-Szczerbo et al. | |
| 4,763,071 | 8/1988 | McGee et al. | |
| 4,771,238 | 9/1988 | Caruso et al. | |
| 4,835,471 | 5/1989 | Kutilin | 324/236 |
| 4,837,511 | 6/1989 | Whittington et al. | |
| 4,879,531 | 11/1989 | Tigges et al. | |
| 5,012,206 | 4/1991 | Tigges | |
| 5,055,784 | 10/1991 | Jaeger et al. | |
| 5,091,696 | 2/1992 | Koosen | |
| 5,119,022 | 6/1992 | Kranbuchi et al. | 324/234 |
| 5,199,545 | 4/1993 | Takamisawa et al. | |

OTHER PUBLICATIONS

RF Inductive Distance Measuring, Sensor Technology, Nov., 1986.
Non-Contact Sensor Satisfies Host of Aerospace Needs, Design News, Dec. 18, 1989.
Smart Sensors To Take Over By 1992, Managing Automation, Jun. 1988.
Handbook of Intelligent Sensors For Industrial Automation, Copyright 1992.
The Analysis Of Eddy Currents, 1974.

Primary Examiner—Walter E. Snow
Attorney, Agent, or Firm—Tarolli, Sundheim & Covell

[57] ABSTRACT

An apparatus for sensing a target characteristic, such as relative distance between the apparatus and target, target thickness, target material, or lateral position between the apparatus and the target, includes a coil for directing an electro-magnetic field at the target. A voltage controlled oscillator energizes the coil at a resonant frequency which is functionally related to the target characteristic. The coil has an effective impedance value at resonance functionally related to the target characteristic. A frequency monitor measures the resonant frequency. An impedance monitor determines the impedance value when the drive frequency is at the resonant value. A PROM or controller determines the target characteristic in response to the measured resonant frequency and the determined impedance value. The PROM or controller provides a signal responsive to the determined target characteristic.

29 Claims, 6 Drawing Sheets

METHOD AND APPARATUS FOR SENSING A TARGET CHARACTERISTIC BY MEASURING BOTH IMPEDANCE AND RESONANT FREQUENCY OF A TANK CIRCUIT

GOVERNMENT RIGHTS

This invention was made with Government support under NASA SBIR Contract NAS8-39315 award by NASA. The Government has certain rights in the invention.

TECHNICAL FIELD

The present invention is directed to an intelligent proximity sensor and is particularly directed to a method and apparatus for sensing a target characteristic.

BACKGROUND OF THE INVENTION

Eddy-current inductive proximity sensors for sensing a specific target characteristic are known in the art. Such characteristics include distance between the sensor and the target, thickness of the target, and target material. The measurements of distance and thickness in an eddy-current inductive type sensor are dependent upon the target material. If an eddy-current inductive type proximity sensor is used as a switch having an "ON" or "OFF" condition to indicate distance from a target, the actual distance at which the switching occurs is dependent upon the target material.

Proximity switch arrangements typically use an inductor coil to direct an electro-magnetic field toward a target. As the target and coil approach each other, the coil experiences a change in both its inductance and resistance as a function of the distance therebetween. The variation is the result of reflection of the induced eddy-currents in the target. It is difficult, however, to measure the change in coil impedance.

Certain known proximity switch arrangements use a Hartley Oscillator to detect a predetermined distance between the target and the coil. The coil impedance is used as an active part of the oscillator circuit. As the distance between the coil and the target decrease, the impedance decreases. At some distance, the impedance decreases below a threshold necessary to keep the oscillator oscillating. When the oscillation stops, a switch is switched "ON." Such an arrangement is subject to component value variations which result in a variation of the threshold value. Variation in the threshold value effects a change in the distance between the coil and the target at which the switch condition changes.

U.S. Pat. No. 5,012,206 discloses an inductive proximity switch arrangement that provides a switching function which occurs at a predetermined distance independent of whether the target material is an electrically conductive nonmagnetic nonferrous metal ("NF") or a ferromagnetic metal ("FE"). To accomplish this function, the oscillator frequency and the impedance of the sensor resonant circuit at the oscillator frequency are respectively set to be equal to a critical frequency and a critical impedance value at a critical response point defined by a point where impedance-frequency characteristic curves of the sensor resonant circuit under the influence of NF objects and FE objects at the predetermined switching distance intersect.

U.S. Pat. No. 4,727,322 discloses an eddy-current sensor used to measure thickness of a test part. The sensor measures two orthogonal components of impedance of the sensor coil. The two orthogonal components are a purely resistive component and a reactive component. The reactive component is frequency dependent. To measure the target thickness, a calibration procedure develops a family of curves over a range of thicknesses under consideration. During actual measurement, the sensor is brought to a distance which results in one of the orthogonal components having a predetermined value. The value of the other component is measured and compared against the calibrated values to determine thickness.

U.S. Pat. No. 4,230,987 discloses an eddy current sensor for monitoring metallurgical contents of an electrically conductive material. A parallel connected coil and variable capacitor are provided. An unknown specimen is inserted into the coil. An alternating voltage is applied to the coil-capacitor combination and the capacitor value is changed in steps. As the capacitor value changes, so does the phase of the voltage across the coil. Phase verses capacitor values of the unknown specimen are compared against phase verses capacitor values of known specimens. A display provides the generic name or grade based upon the matched phase values.

SUMMARY OF THE INVENTION

The present invention provides a method and apparatus for determining at least one of several target characteristics. The apparatus includes a coil driven at a resonant frequency. While at resonance, impedance of the coil is determined. The values of the resonance frequency and the coil impedance, while the coil is being driven at the resonance frequency, are both functionally related to the target characteristics. A memory device or control device determines the target characteristic from the resonant frequency and the coil impedance and provides a control signal in response thereto.

In accordance with one aspect of the present invention, an apparatus is provided for sensing a target characteristic and for providing an electrical signal in response to the sensed target characteristic. The apparatus comprises coil means for directing an electro-magnetic field at the target. The coil means has an effective impedance value functionally related to the target characteristic. Energizing means is drivably coupled to the coil means for energizing the coil means at a resonant frequency functionally related to the target characteristic. Means are provided for measuring the resonant frequency of the coil means. Means are provided for determining the impedance value when the frequency is at its resonant value. Means are provided for determining the target characteristic in response to the measured resonant frequency and the determined impedance value at resonance. The apparatus further includes means responsive to the determined target characteristic for providing the signal responsive to the target characteristic.

In accordance with another aspect of the present invention, a method is provided for sensing a target characteristic and providing an electrical signal in response to the sensed target characteristic. The method comprises the step of directing an electro-magnetic field at the target with a coil. The coil has an effective impedance value functionally related to the target characteristic. The method further comprises the steps of energizing the coil at a resonant frequency functionally related to the target characteristic, measuring the resonant frequency of the coil, and determining the impedance value when the frequency is at its resonant value. The method further includes determining the target characteristic in response to the measured resonant frequency and the determined impedance value at resonance. An electric signal is provided in responsive to the determined target characteristic.

A sensor assembly in accordance with the present invention provides measurements of target characteristics including (1) relative distance between the sensor and the target, (2) relative distance and relative lateral position between the sensor and the target, (3) target material, and (4) target thickness. A proximity switch in accordance with the present invention permits a switching condition (1) at a predetermined relative distance between the sensor coil and the target which is functionally related to the target material, or (2) at a predetermined relative distance between the sensor coil and the target independent of the target material.

BRIEF DESCRIPTION OF THE DRAWINGS

Other features and advantages of the present invention will become apparent to those skilled in the art to which the present invention relates from a reading of the following detailed description of preferred embodiments with reference to the accompanying drawings, in which.

DESCRIPTION OF PREFERRED EMBODIMENTS

Figure 1:
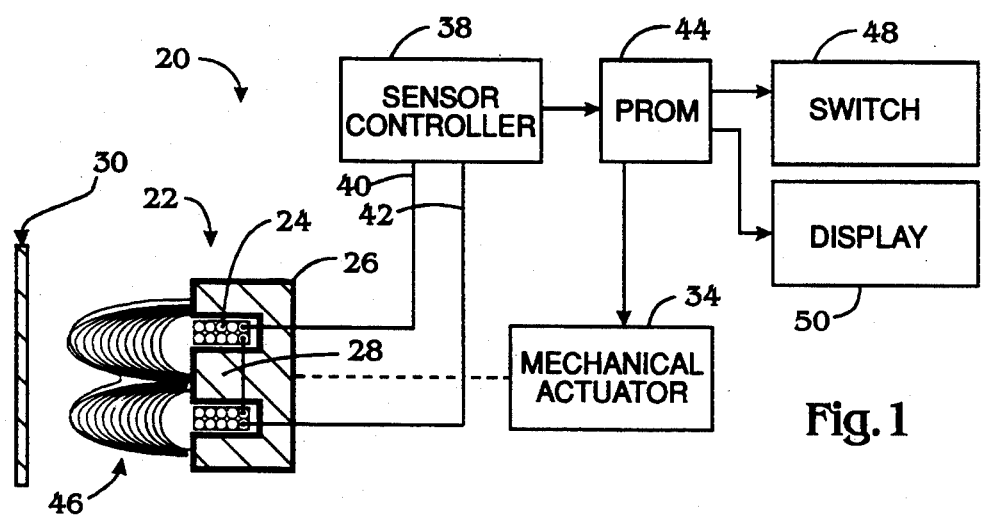
FIG. 1 is a schematic block diagram of an apparatus for sensing a target characteristic made in accordance with the present invention.

Referring to FIG. 1, a sensor apparatus 20 includes a coil 22 having wire 24 wound on coil form 26. The coil form is a cup or pot core having a center post 28. The coil form 26 is made of a ferrite material. The coil 22 is movable relative to a metallic target 30 by a mechanical actuator 34 drivably connected thereto. A mechanical actuator is shown for purposes of explanation only to provide a means for changing the distance between the coil 22 and a target. Such a mechanical actuator may take the form of a robot arm. In another contemplated arrangement, the coil is mounted to a stationary fixture and the target moves toward or passed the coil.

The coil 24 is electrically connected to a sensor controller 38 via wires 40, 42. When the coil 22 is energized with an alternating current ("AC") signal, an electromagnetic field 46 is produced. The coil form 26 is, as mentioned, preferably cup shaped with a center post, although other forms may be used. The coil wire 24 is wound on the center post 28 of the coil form 26 so that the resultant electro-magnetic field 46 is directed toward the target 30. When the field 46 acts upon the target 30, eddy-currents are established in the target. These eddy-currents are reflected by the target and effect a change in inductance and resistance of the coil 22.

The sensor controller 38 is connected to a programmable-read-only-memory ("PROM") 44. The PROM 44 is controllably connected to the mechanical actuator 34 for control of the relative position between the coil 22 and the target 30 as a function of a target characteristic, to a switch 48 for controlling the switch state as a function of a target characteristic, and/or to a display 50 for displaying information regarding a target characteristic. Such target characteristics include (1) relative distance between the sensor coil and the target, (2) relative distance and relative lateral position between the sensor coil and the target, (3) target material, and (4) target thickness. If the controller 38 controls a switch, the controller controls the switching condition (1) at a predetermined relative distance which is functionally related to the target material, or (2) at a predetermined relative distance independent of the target material.

Figure 2:
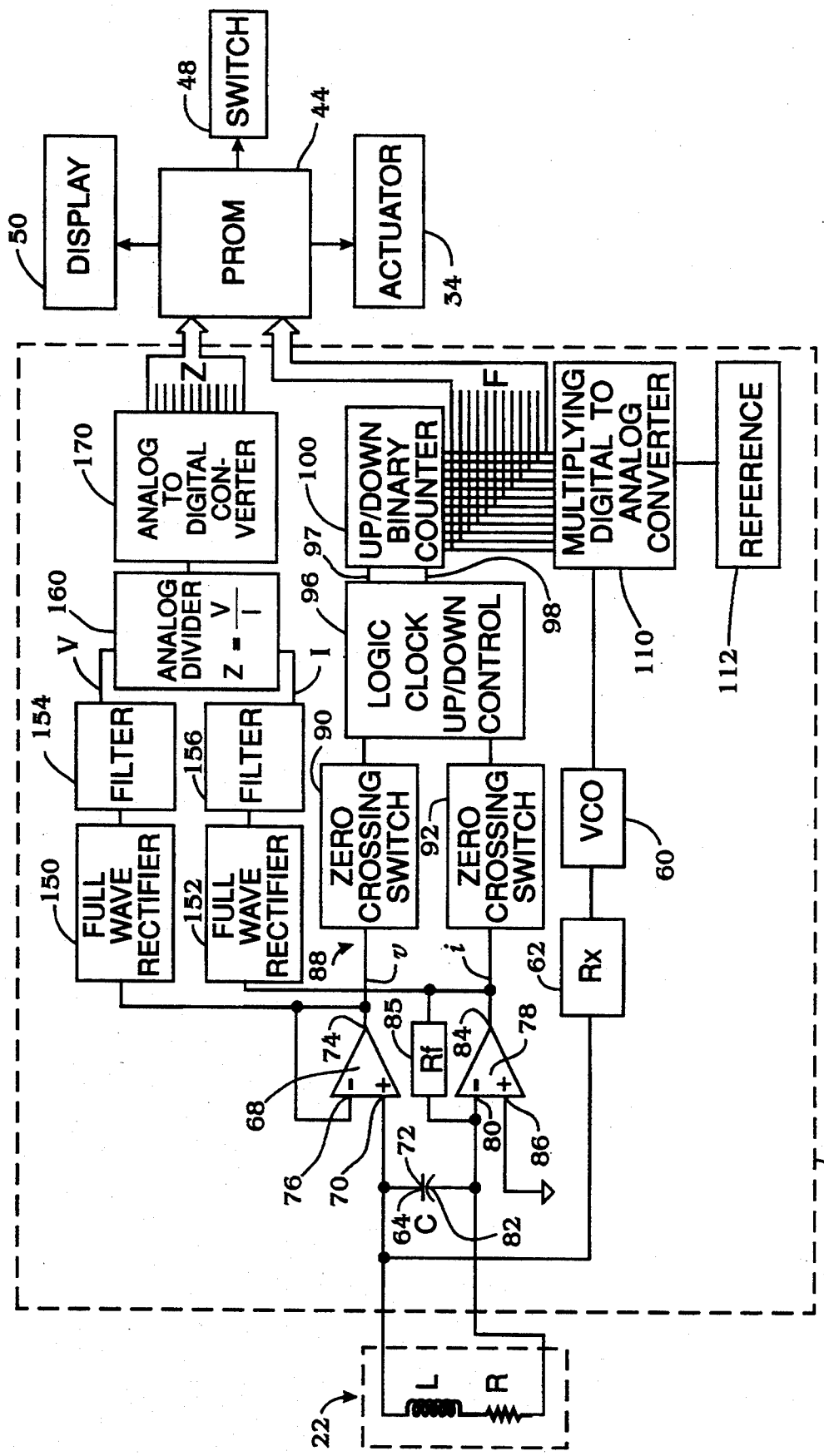
FIG. 2 is a schematic block diagram of the apparatus of FIG. 1 with the sensor controller shown in greater detail.

Referring to FIG. 2, the coil 22 has a total effective inductance L resulting from both the coil and the effect of the reflected eddy currents from the target. The coil also has an effective impedance R. The sensor controller 38 includes a voltage-controlled-oscillator ("VCO") 60 connected to the coil 22 through a resistor 62 having a known resistance value Rx. A capacitor 64, having a capacitance value C, is connected in parallel across the coil 22. The parallel connected capacitor 64 and coil 22 form a tank circuit. The VCO 60 is used to drive the tank circuit with an AC signal.

The sensor controller 38 determines "real" and "imaginary" components of the coil impedance. To accomplish this determination, the VCO 60 drives the tank circuit at a resonant frequency. When the frequency of the VCO 60 is set to exactly the resonant frequency, the total impedance of the parallel C/RL circuit is purely resistive. When the frequency is less than the resonant value, the resonant circuit acts like a R-L series circuit. When the frequency is greater than the resonant value, the resonant circuit acts like a R-C series circuit. When the frequency of the drive signal from the VCO is at the resonance value, current "i" through the coil 22 is exactly in phase with the voltage "v" developed across the coil 22.

The resistor 62 in series with the coil 22 forms a resistor divider network making the resistance of the coil 22 easier to measure. At the resonance frequency, the combined inductive reactance of the resonant circuit equals the capacitive reactance of the circuit but 180 degrees out of phase thereby giving a pure resistance value. Since the value of the capacitor in the tank circuit is fixed and the inductance varies as a function of the distance, material, and thickness of the target, the value of the resonance frequency is determined by the inductance itself. Therefore, the VCO can be adjusted so as to make the v and i signals in phase. The frequency at resonance, designated "F" is indicative of the inductance which is, in turn, indicative of the distance, material, and thickness of the target. Also, once in phase, the resistance of the tank circuit, designated "Z" is equal to v/i.

An amplifier 68 has its non-inverting input 70 connected to one side 72 of the capacitor 64. The output 74 of the amplifier 68 is connected to the inverting input 76 of the amplifier 68 so as to form a voltage follower circuit. The amplifier 68 has a high input impedance thereby eliminating a coupling effect with the resonating tank circuit. The output of the amplifier 68 is the voltage value v developed across the coil 22.

An amplifier 78 has its inverting input 80 connected to the other side 82 of the capacitor 64. The output 84 of the amplifier 78 is connected to the inverting input 80 of the amplifier 78 through a resistor 85 having a resistance value Rf. The non-inverting input 86 of amplifier 78 is connected to ground. The amplifier 78 is connected so as to form a current follower or a current to voltage converter circuit. The amplifier 78 has essentially a zero ohms input impedance thereby having no effect on the voltage measurement v. The output of the amplifier 78 is a value of the current i through the coil.

Figure 3A:
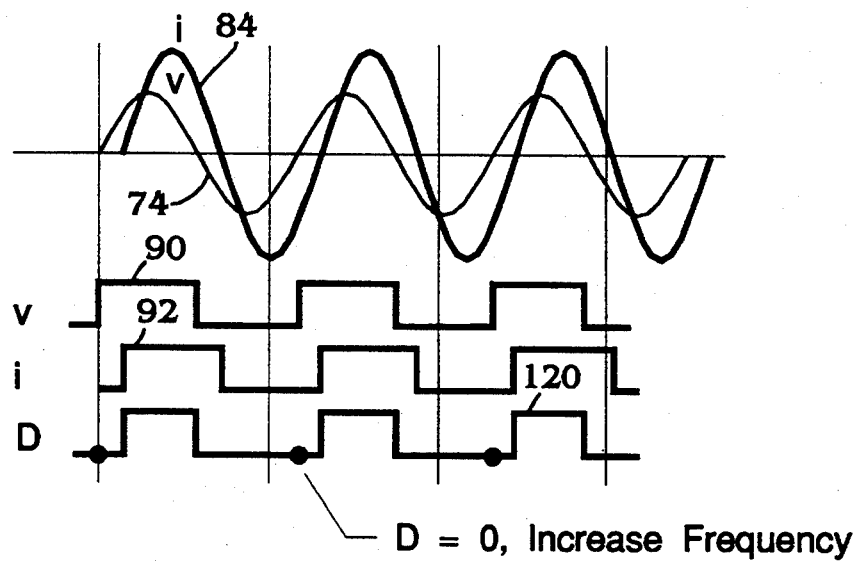
FIGS. 3A-3C are graphical representations of several electrical signals of the apparatus of FIG. 1 while in operation.
Figure 3B:
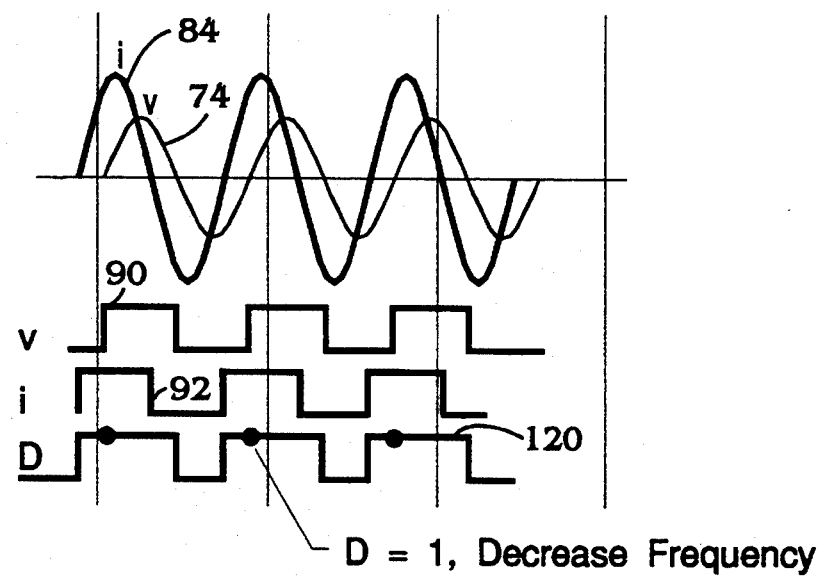
Figure 3C:
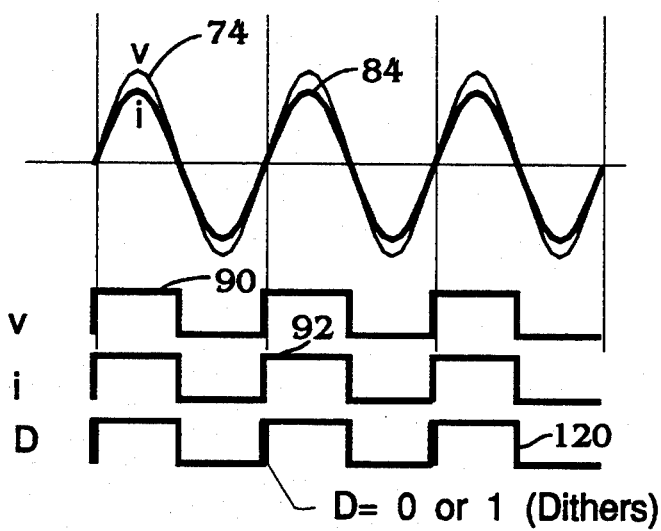

FIGS. 3A-3C show the various relative conditions of the current i through the coil 22 and the voltage v developed across the coil 22. FIG. 3A shows a condition when the current i lags behind the voltage v. In FIG. 3A, the current i is the output 84 of amplifier 78. The voltage across the coil is the output 74 of amplifier 68. FIG. 3B shows a condition when the current i is ahead of the voltage v. FIG. 3C shows a resonant condition when the current i and the voltage v are substantially in phase. As mentioned, it is desirable to have the coil 22 driven at resonance to be able to determine the true resistance R and the true inductance L of the coil so as to provide a determination of target characteristics.

The outputs of the amplifiers 68, 78 are connected to a phase detector circuit 88. Specifically, the output 74 of the amplifier 68 is connected to a zero crossing switch 90. The output 84 of the amplifier 78 is connected to a zero crossing switch 92. The zero crossing switches 90, 92 respectively convert each of the output signals 74, 84 into binary values of "1" if the value of the output signal of the associated amplifier is positive and "0" if the output signal of the associated amplifier is negative. This essentially converts the sine-wave output signals of v and i from the amplifiers 68, 78, respectively, into square waves.

The outputs of the zero crossing switches 90, 92 are connected to a logic clock 96. The logic clock 96 timewise compares the phase of the v and i signals. The outputs of the logic clock 96 are connected to a 12 bit, binary up/down counter 100. Specifically, the logic clock circuit 96 has a direction control output 97 connected to a direction control input of the counter 100. The logic clock circuit 96 also has a clock output signal 98 connected to the clock input signal of the counter 100. Upon comparing the relative phase of the v and the i signals, the logic clock 96 outputs an up count command on line 97 and a count pulse on line 98 if v occurs before i. If i occurs before v, the clock 96 outputs a down command on line 97 and a count pulse on line 98. Each time the up command is output and a count pulse is output, the counter counts up. Each time the down command is output and a count pulse is output, the counter counts down.

Changes in the output of the counter 100 are indicative of the relative phase between v and i. The output of the counter 100 is referred to as the F count. The output of the counter 100 is connected to a multiplying digital-to-analog ("D/A") converter 110. A reference voltage 112 is connected to the D/A converter for its proper operation as is well known in the art. The output of the D/A converter 110 is connected to the control input of the VCO 60. The output of the D/A converter is an analog control signal for the VCO 60. In a preferred embodiment, a F count value of 000000000000 results in an output voltage of −10 VDC from the D/A converter 110. An F count value of 111111111111 results in an output voltage of +10 VDC from the D/A converter 110. This closed loop control arrangement is stabilized when the VCO drives the coil at resonance, i.e., when v and i are in phase. Therefore, the F count is indicative of the resonant frequency.

Referring to FIGS. 3A-3C, various conditions of the relative phase between v and i are depicted. When the VCO frequency is less than the resonant value, the i curve lags the v curve, which is the condition shown in FIG. 3A. The outputs of the zero crossing switches 90, 92 are shown below the analog v and i curves with the same time scale x-axis. Since the i signal from switch 92 goes HIGH after the v signal goes HIGH from switch 90, the logic clock 96 outputs an up command to increase the frequency of the VCO 60.

Figure 4:
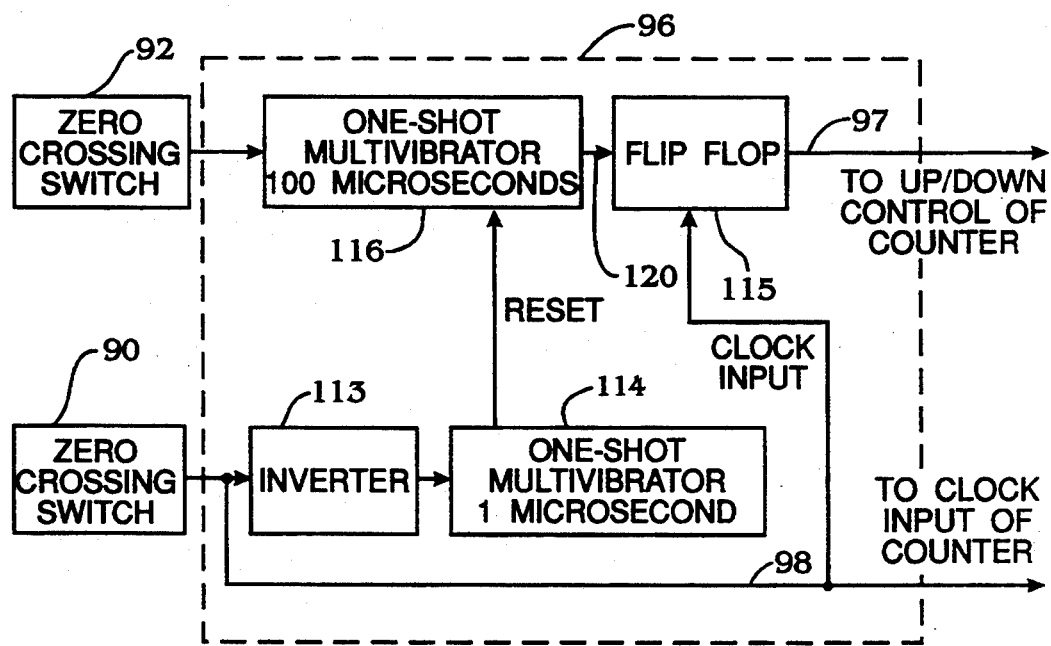
FIG. 4 is a schematic block diagram of the logic clock shown in FIG. 2.

Referring to FIG. 4, the logic clock 96 includes an inverter 113 connected to the output of the zero crossing switch 90. The output of the zero crossing switch 90 is the clock output 98 of the clock circuit 96 and is directly connected to the clock input of the counter 100. The output of the zero crossing switch 90 is also connected to the clock input of a FLIP-FLOP 115. The output of the inverter 113 is connected to an input of an one shot multivibrator 114. The clock 96 further includes a one shot multivibrator 116 having its input connected to the output of the zero crossing switch 92. The output 120 of the one shot 116 is connected to the reset/set input of the FLIP-FLOP 115. The output 120 is a direction request line. The output of the one shot 114 is connected to the reset input of the one shot 116. The output 97 of the FLIP-FLOP 115 is the direction control signal connected to the direction control input of the counter 100. The FLIP-FLOP 115 functions as a latch to latch the direction request on line 120 at the sample time controlled by the output of the zero crossing switch 90.

With this arrangement, the output 120 of the one shot 116 (the direction request line) goes HIGH upon the rising edge of the output 92 for the signal i and goes LOW upon the falling edge of the output 90 for the signal v. The signal 120 is then sampled at the occurrence of the leading edge of the output 90 of the signal v. The FLIP-FLOP 115 latches the direction request value (a HIGH or a LOW) present at its set/reset input upon the occurrence of a rising edge of the line 98. The value latched at the sample time is use to provide the direction control signal 97 for the up/down counter 100.

In FIG. 3A in which the i curve lags the v curve, meaning that the frequency is too low, the signal 120 from the one shot 116 at the sample time is LOW which results in a LOW being latched into the FLIP-FLOP. The output line 97 would then be LOW which commands the counter 100 to count up. This count up signal results in an increase in the output frequency of the VCO 60.

Referring to FIG. 3B, the current curve i is ahead of the voltage curve v meaning that the frequency is greater than resonance. The outputs 90, 92 of the switches result in the signal 120 being HIGH at the sample time which results in a HIGH being latched into the FLIP-FLOP 115 upon the occurrence of the leading edge of the v signal. The output of the FLIP-FLOP is then HIGH or a 1, meaning that the frequency is greater than resonance. A HIGH on the command line 97 results in a count down command to the up/down counter 100 so as to result in a decrease in the frequency of the VCO 60.

The counter logic clock 96, the counter 100, the D/A converter 110, and the VCO 60 are arranged so that a count up signal from the logic clock 96 results in an increase in the frequency output from the VCO 60. Similarly, a count down signal from the logic clock 96 results in a decrease in the frequency output from the VCO 60.

Referring to FIG. 3C, the current curve i and the voltage curve v are shown as in-phase. When this occurs, the value of the output 120 from the one shot 116 dithers or oscillates between HIGH and LOW upon the occurrence of alternate latch pulses to the FLIP-FLOP. This results in the output of the FLIP-FLOP to dither causing the count output F from the binary up/down counter 100 to repeatedly dither up one count or down one count when resonant frequency is achieved. When the output of the counter 100 is dithering about the resonant frequency, the output of the D/A converter 110 is also dithering. The frequency output from the VCO 60 is held substantially constant at the resonant frequency.

The VCO 60 provides internal filter of the D/A output signal so as to smooth out the dither variations. When the coil 22 is driven at resonance, the impedance of the coil 22 is determined. The count F, which is indicative of the resonant frequency of the coil 22, is connected to the PROM 44.

The output of the amplifier 68 is connected to a full wave rectifier circuit 150. The output of the amplifier 78 is connected to a full wave rectifier circuit 152. The output of the rectifier 150 is connected to a filter circuit 154. The output of the rectifier 152 is connected to a filter circuit 156. The filter circuits 154, 156 are preferably RC filter circuits that, respectively, full wave rectify the signals v and i. The output of the rectifier 154 is a DC signal having a value V functionally related to the value of v. The output of the rectifier 156 is a DC signal having a value I functionally related to the value of i. The outputs of the filters 154 and 156 are connected to an analog divider circuit 160 that determines a value Z equal to V/I and outputs an analog signal having a value functionally related to the value of V/I.

The output of the analog divider 160 is connected to an analog-to-digital ("A/D") converter 170. The output of the A/D converter is a digital value Z having a value functionally related to the value of the effective impedance of the coil 22 in Ohms. The A/D converter is preferably a twelve-bit converter that provides a twelve bit digital word. In an preferred embodiment, the value 111111111111 represents 11,260 Ohms and the value 000000000000 represents 0 Ohms.

The digital word F is referred to as the F count. The digital word Z is referred to as the Z count. The F count and the Z count include information indicative of several characteristics of a target in the sensor coil's range. These characteristics include (i) relative distance between the coil and the target, (ii) target material, (iii) target thickness, and (iv) relative distance and the relative lateral position between the coil 22 and the target. The output F count and Z count are connected to the PROM 44.

The PROM 44 includes empirically determined data that relates values of F count and Z count information for the target characteristic desired. The PROM compares or correlates the stored values against measured values and provides and output signal in response to the comparison. The output signal from the PROM can be used to control a display, a switch, and/or an actuator. As those skilled in the art appreciate, the PROM may be replaced by a microcomputer programmed to interpret the F count and the Z count information and control a display, a switch, and/or an actuator in response to the interpreted information. Preferably, the sensor controller 38 is manufactured in a single Application Specific Integrated Circuit ("ASIC").

Figure 5:
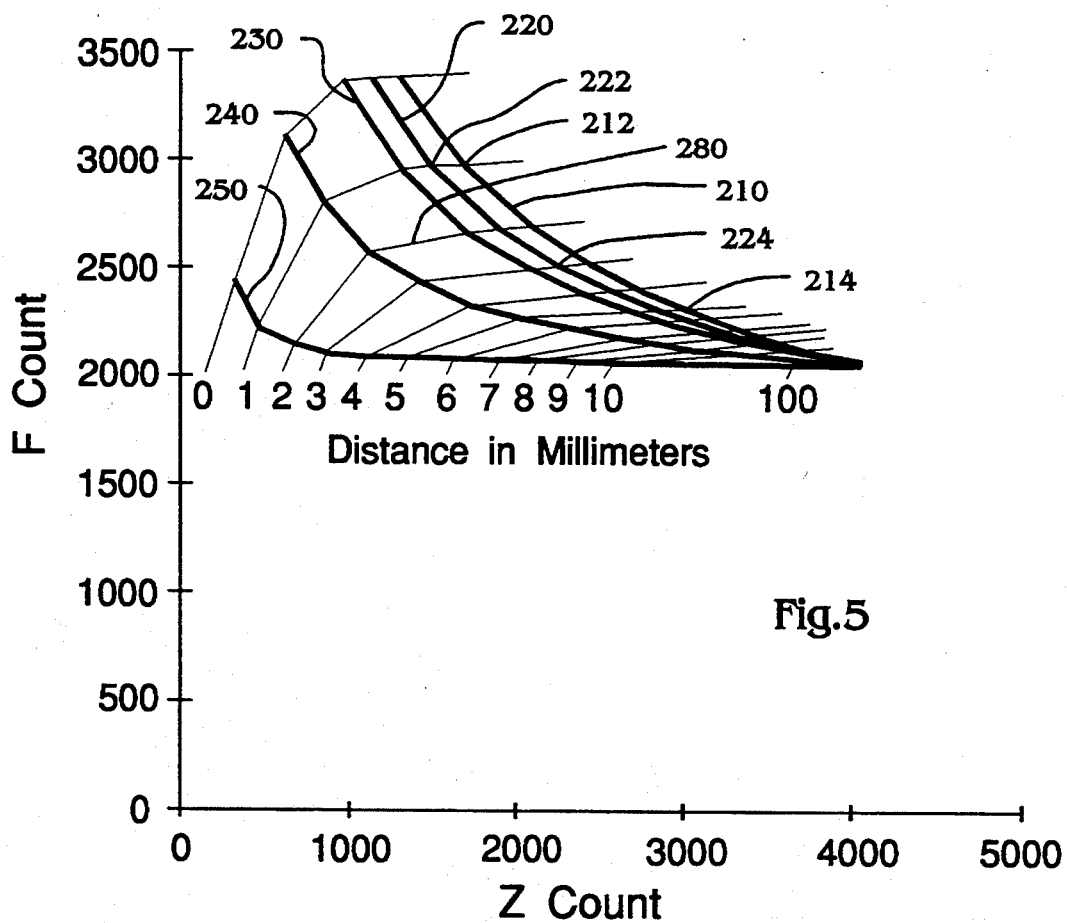
FIG. 5 is a graphical representation of target characteristics as a function of the values of certain electrical signals of the apparatus shown in FIG. 1.

Referring to FIG. 5, a graph is shown of stored F count values on the Y-axis and the Z count values on the X-axis for different target materials at varying distances between the coil 22 and the target 30. These values are empirically determined. Line 210 represent F count and Z count information for a target made from copper. Point 212 on line 210 represents the F count value and the Z count value when the copper target is 1 millimeter from the coil 22. Point 214 on line 210 represents the F count value and the Z count value when the copper target is 5 millimeters from the coil 22. Line 220 represents F count and Z count information for a target made from aluminum. Point 222 on line 220 represents the F count value and the Z count value when the aluminum target is 1 millimeter from the coil 22. Point 224 on line 220 represents the F count value and the Z count value when the aluminum target is 3 millimeters from the coil 22. Line 230 represents F count and Z count information for a target made from brass. Line 240 represents F count and Z count information for a target made from stainless steel. Line 250 represents F count and Z count information for a target made from steel.

From the F count and Z count information contained in the graph of FIG. 5, several control arrangements are possible. When arranged to function as a proximity switch, the PROM 44 is connected only to the switch 48. Several types of proximity switches are possible using the apparatus of the present invention. In accordance with one embodiment of the present invention, a proximity switch is provided that changes switch conditions when the distance between the target and the coil reach a predetermined value independent of the target material. This is accomplished by storing the F count information and the Z count information into the PROM for the predetermined switching distance for all anticipated target materials the sensor may encounter. This information may be obtained using empirical methods. For example, the F count information and the Z count information for samples on the 2 millimeter distance line 280 are stored in the PROM 44. Line 280 represents the F count information and the Z count information for a target being 2 millimeters away. If the F count and Z count information is to the left of or above the values defined by line 280, the switch 48 is set or commanded by the PROM to one condition. If the F count and Z count information is to the right of or below the values defined by line 280, the switch 48 is set or commanded by the PROM to another condition.

In accordance with another embodiment of the present invention, the PROM 44 is programmed to change the switch condition when a particular target material comes within a predetermined distance of the coil and ignoring all other materials that may be present. To accomplish this feature, the PROM is programmed with the F count and Z count information for one material only such as the line 240 for stainless steel. If the switching distance selected is 3 millimeters for stainless steel, the switch would be set or commanded by the PROM to one condition if the F count and the Z count information was on the right side of the 3 millimeter point and on the line 240. The switch would be set or commanded by the PROM to the other condition if the F count and the Z count information was on the left side of the 3 millimeter point and on the line 240. Data not being on the line 240 is ignored for switch position control.

The sensor apparatus 20, in accordance with yet another embodiment of the present invention, provides an indication of both material and distance. In this embodiment, the PROM 44 is connected to a display 50. The PROM 44 is programmed with the F count and Z count information contained in graph of FIG. 5. The PROM monitors the F count and Z count information and compares the information with that it has stored. Based on correlation of data between measured and stored F count and Z count information, the PROM 44 outputs to the display an electric signal indicative of target material and target distance from the coil.

In accordance with another embodiment of the present invention, the sensor is used to control a mechanical actuator 34 such as a robot arm. In this embodiment, the PROM 44 is connected to the actuator 34. The PROM is programmed with actuator control signals as a function of target distance and/or material. For example, if the robot is controlling a tool at the end of its arm, a sensor apparatus made in accordance with the present invention controls distance between the end of the arm and the target.

Figure 6:
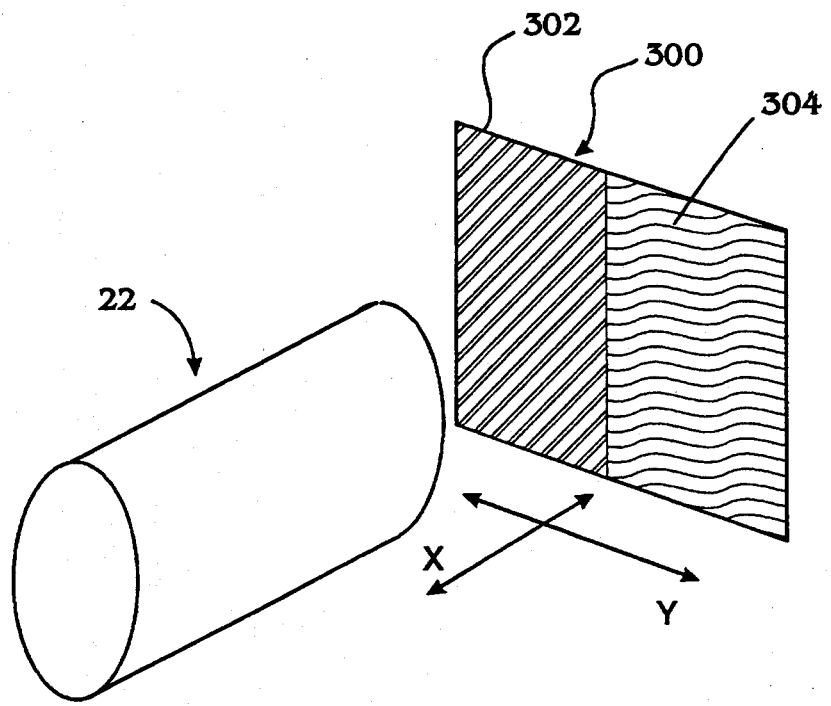
FIG. 6 is a schematic representation of the coil of FIG. 1 spaced from a target which is made of two separate materials.
Figure 7:
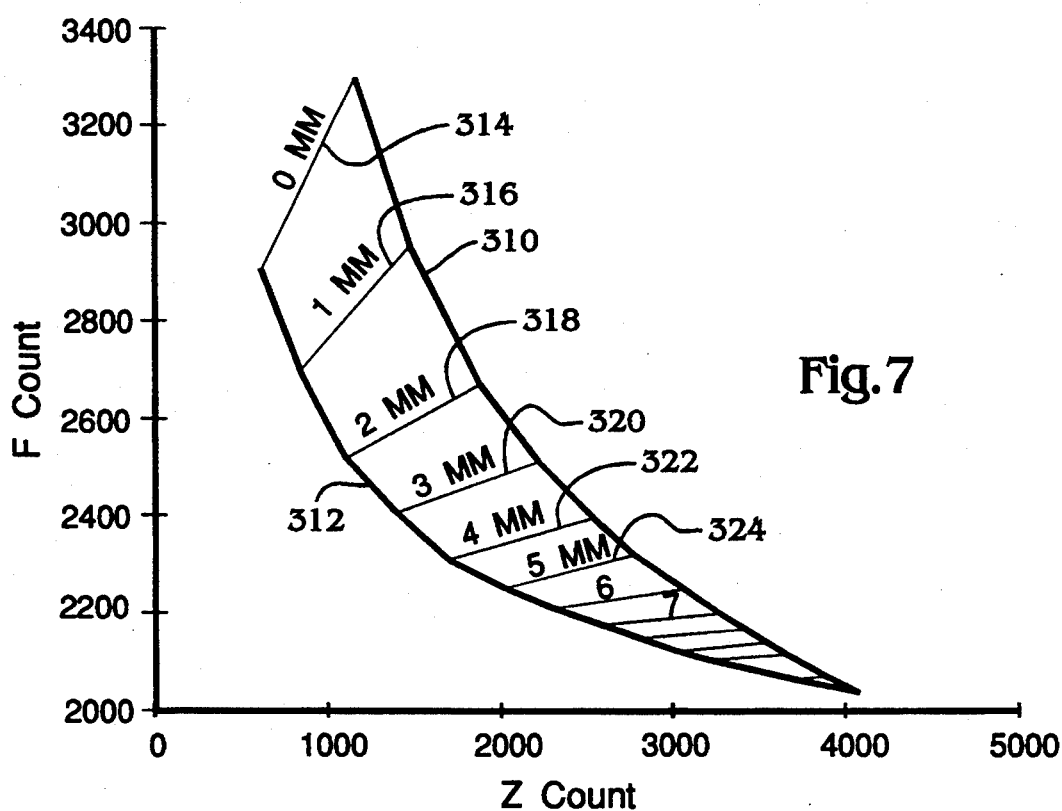
FIG. 7 is a graphical representation of relative distance and lateral displacement between the coil and target of FIG. 6 as a function of the values of certain electrical signals of the apparatus shown in FIG. 1.

Referring to FIGS. 6 and 7, an arrangement is shown to determine the lateral position between the sensor coil 22 and a compound target 300 made of at least two different materials 302, 304. The coil 22 is located a distance X from the target. Lateral movement of the coil is indicated as being along the Y axis. Line 310 in FIG. 7 represents the F count and the Z count values for different distances between the coil and target when the coil 22 is laterally aligned with the target material 302 made from aluminum. Line 312 in FIG. 7 represents the F count and the Z count values for different distances between the coil and the target when the coil 22 is laterally aligned with the target material 304 made from stainless steel. Lines 314, 316, 318, 320, 322, 324, etc., are the F count and Z count information when the associated distance between the coil and the target is held constant at a value associated with one of those lines with the coil laterally traversing across the target. In accordance with another embodiment of the present invention, the PROM 44 includes the information included in the graph of FIG. 7. A switch is controlled as a function of the relative lateral position between the coil and the target or as a function of both relative lateral position and relative distance between the coil and the target. Such distance and lateral position information can also be displayed. This arrangement provides a sensor that senses proximity in two directions, i.e., perpendicular and lateral relative to the target.

Figure 8:
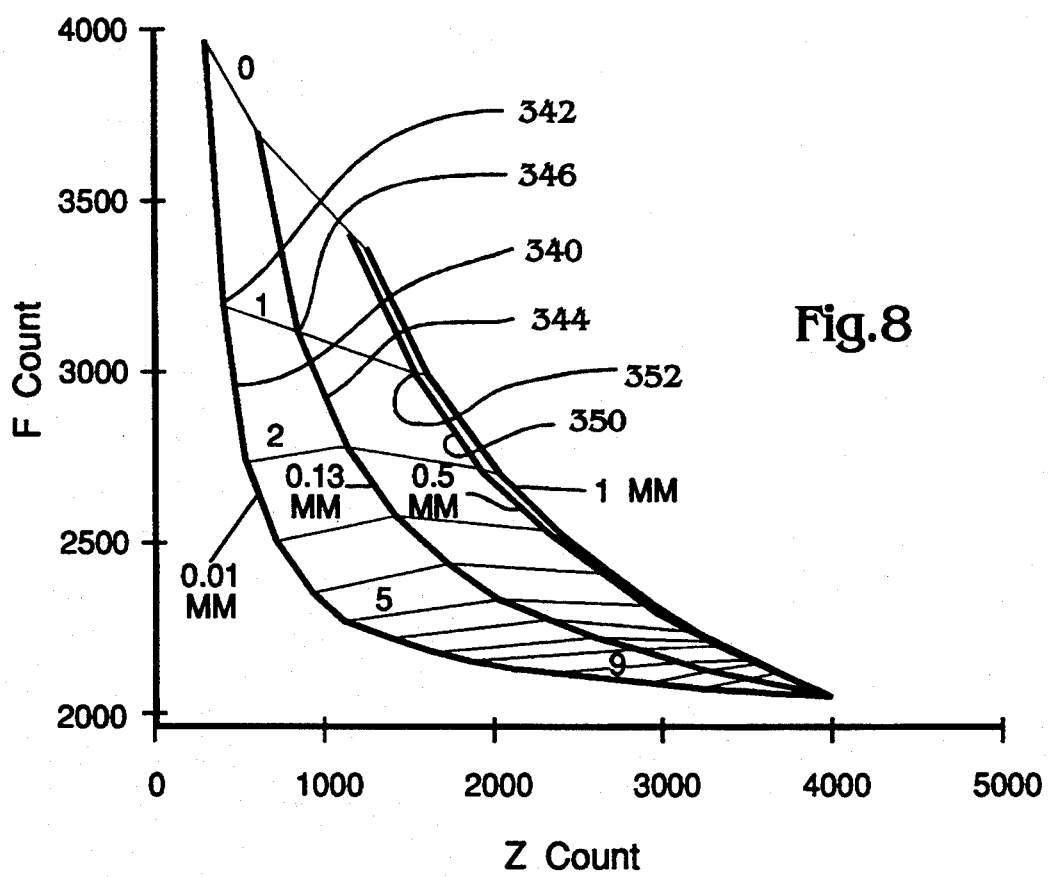
FIG. 8 is a graphical representation of target thickness and relative distance between the coil and target as a function of the values of certain electrical signals of the apparatus shown in FIG. 1.

In accordance with still yet another embodiment of the present invention, the sensor provides an indication of target thickness. Referring to FIG. 8, the F count and Z count information for targets made of a material of interest having different thicknesses is empirically determined and stored for different relative distances between the target and the coil. Line 340 is the F count and the Z count information for an aluminum target having a thickness of 0.01 millimeters and located at various distances from the coil. Point 342 on line 340 is the 0.01 millimeter thick target located a distance of 1 millimeter from the coil. Line 344 is the F count and the Z count information for an aluminum target having a thickness of 0.13 millimeters and located at various distances from the target. Point 346 on line 344 is the 0.13 millimeter thick target located a distance of 1 millimeter from the coil. Line 350 is the F count and the Z count information for an aluminum target having a thickness of 0.50 millimeters and located at various distances from the target. Point 352 on line 350 is the 0.50 millimeter thick target located a distance of 1 millimeter from the coil.

In accordance with this thickness sensing embodiment of the present invention, the PROM 44 includes the information included in the graph of FIG. 8. A switch is controlled as a function of material thickness or as a function of both target thickness and relative distance between the coil and the target. Such information can also be displayed or used to control a mechanical actuator.

Figure 9:
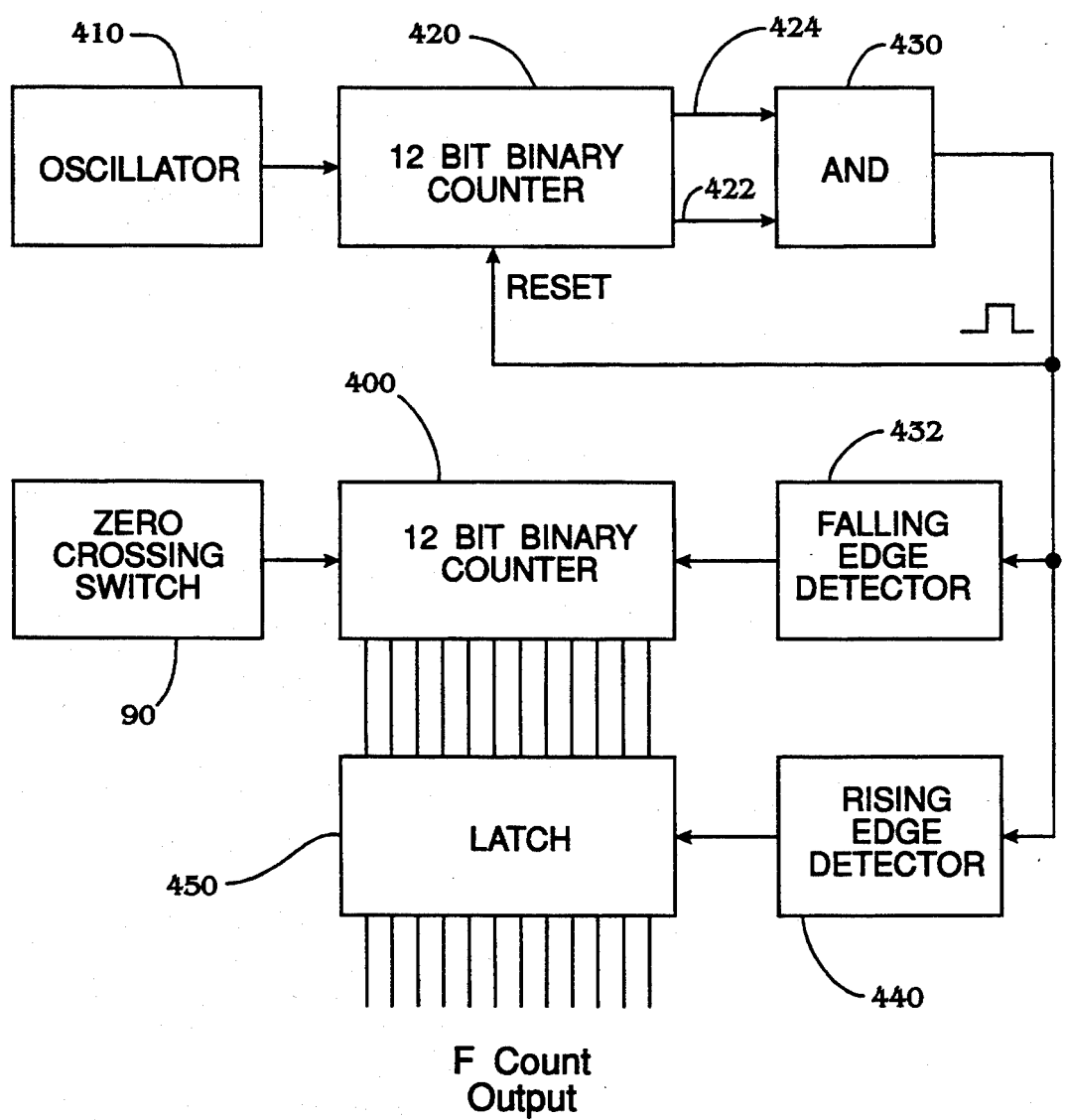
FIG. 9 is a schematic block diagram showing an alternative circuit for determining the F count information for the apparatus shown in FIG. 1.

FIG. 9 depicts an alternative arrangement for determining an F count value that would be substantially temperature insensitive. The ratio of the control input to the frequency output of a voltage control oscillator is not typically temperature stable. If the VCO output frequency varies with temperature, the F count from counter 100 will vary to keep the closed loop "satisfied," i.e., to keep v and i in phase. To obtain a more temperature stable F count, the output of zero crossing switch 90 is also connected to a 12 bit, binary counter 400. An oscillator 410 is connected to a 12 bit binary counter 420. Two bits 422, 424, from the counter 420 are respectively connected to an AND gate 430. The output of the AND gate 430 is connected to the reset input of the counter 420. If the oscillator 410 outputs a 10 kilohertz frequency and output lines 424 and 422 of counter 420, representing the 64th and the 256th bit count, respectively, are ANDED in the AND gate 430, a reset pulse is provided by the AND gate 430 every 32 milliseconds. This reset pulse is a HIGH true pulse, i.e., normally LOW. The output of the AND gate 430 is connected to a falling edge detector 432. The falling edge detector 432 is connected to the counter 400. The output of the AND gate 430 is also connected to a rising edge detector 440. The output of the rising edge detector is connected to the clock input of a latch 450. The latch 450 is connected to the output of the binary counter 400. The output of the latch 450 is used as the F count information. With this arrangement, the frequency of the signal used to drive the coil is measured by monitoring the frequency of the voltage v developed across the coil 22. The frequency count held in the latch 450 is updated each time the reset pulse from the AND gate 430 is provided. With this arrangement, the frequency monitoring is not part of the closed loop control thereby eliminating variations that would other wise result from temperature effects on the VCO.

This invention has been described with reference to preferred embodiments. Modifications and alterations may occur to others upon reading and understanding this specification. It is my intention to include all such modifications and alterations insofar as they come within the scope of the appended claims and the equivalents thereof.

Having fully described the invention, the following is claimed:

1. An apparatus for sensing a target characteristic and for providing an electrical signal in response to said sensed target characteristic, said apparatus comprising:
   coil means for directing an electro-magnetic field at said target, said coil means having an effective impedance value functionally related to said target characteristic;
   energizing means drivably coupled to said coil means for energizing said coil means at a resonant frequency functionally related to said target characteristic;
   means for measuring said resonant frequency of said coil means;
   means for determining said impedance value when said frequency is at its resonant value;
   means for determining said target characteristic in response to said measured frequency and said determined impedance value; and
   means responsive to said determined target characteristic for providing said signal responsive to said characteristic.

2. The apparatus of claim 1 wherein said target characteristic is target material.

3. The apparatus of claim 1 wherein said target characteristic is relative distance between said coil means and said target.

4. The apparatus of claim 1 wherein said target characteristic is target thickness.

5. The apparatus of claim 1 wherein said target is made from at least two different materials and wherein said target characteristic is relative lateral position between said coil means and said target.

6. The apparatus of claim 1 wherein said coil means includes a parallel connected coil and capacitor.

7. The apparatus of claim 6 further including a cup core that focuses said electro-magnetic field toward said target.

8. The apparatus of claim 1 further including a switch operatively connected to said electrical signal provided in response to said target characteristic, a condition state of said switch being responsive to said determined target characteristic.

9. The apparatus of claim 8 wherein said target characteristic is relative distance between said coil means and said target.

10. The apparatus of claim 8 wherein said target characteristic is target thickness.

11. The apparatus of claim 8 wherein said target characteristic is target material.

12. The apparatus of claim 8 wherein said target is made of at least two different materials and wherein said target characteristic is relative lateral orientation of said coil means and said target.

13. The apparatus of claim 1 wherein said coil means includes a parallel connected coil and capacitor and wherein said means for energizing includes a voltage controlled oscillator connected to said coil and means for controlling said voltage controlled oscillator at said resonant frequency.

14. The apparatus of claim 13 wherein said means for controlling said voltage controlled oscillator includes means to apply a control voltage to a control input of said voltage controlled oscillator so as to maintain current through said coil in phase with voltage developed across said coil.

15. The apparatus of claim 14 wherein said means for determining said impedance value includes a series connected resistor connected in series with the parallel connected coil and capacitor, means for measuring the voltage drop across said coil, means for measuring the current through said coil, and means for determining effective impedance as a function of sensed voltage and sensed current.

16. The apparatus of claim 15 wherein said means for determining the impedance from said sensed current through said coil and from said voltage developed across said coil includes means for dividing the sensed developed voltage by the sensed current through said coil.

17. The apparatus of claim 1 further including display means connected to said signal responsive to said target characteristic for displaying information indicative of said target characteristic.

18. The apparatus of claim 1 further including mechanical actuator means connected to said signal responsive to said target characteristic for providing relative movement between said coil means and said target in response to said target characteristic.

19. An apparatus for sensing a target characteristic and for providing an electrical signal in response to said sensed target characteristic, said apparatus comprising:
   coil means for directing an electro-magnetic field at said target, said coil means having an effective impedance value and an inductance value functionally related to said target characteristic;
   energizing means drivably coupled to said coil means for energizing said coil means with an alternating current signal at a frequency functionally related to said target characteristic, said energizing means including means for monitoring a voltage developed across said coil means and for monitoring current through said coil means, and means for controlling said alternating current signal frequency so that substantially no phase difference exists between said developed voltage across said coil means and said current through said coil means, said controlled alternating current frequency being said resonant frequency of said coil means;
   means for measuring said resonant frequency of said coil means;
   means for determining said impedance value of said coil means when said frequency of said alternating current signal is at the resonant value;
   means for determining said target characteristic in response to said measured frequency and said determined impedance value; and
   means responsive to said determined target characteristic for providing said signal responsive to said target characteristic.

20. An apparatus for sensing a target characteristic and for providing an electrical signal in response to said sensed target characteristic, said apparatus comprising:
   coil means for directing an electro-magnetic field at said target, said coil means having an effective impedance value and an inductance value functionally related to said target characteristic;

a capacitor connected in parallel with said coil means;

a resistor connected in series with said coil;

energizing means drivably coupled to said coil means through said resistor for energizing said coil means with an alternating current signal at a frequency functionally related to said target characteristic, said energizing means including a voltage controlled oscillator, means for monitoring a voltage developed across said coil means, means for monitoring current through said coil means, and means for controlling said voltage controlled oscillator so that substantially no phase difference exists between said developed voltage across said coil means and said current through said coil means, the output of said voltage controlled oscillator being a resonant frequency of said coil means when said no substantial phase difference exists;

means for measuring said resonant frequency of said coil means;

means for determining said impedance value when said frequency of said alternating current signal is at the resonant value;

means for determining said target characteristic in response to said measured resonant frequency and said determined impedance value; and means responsive to said determined target characteristic for providing said signal responsive to said target characteristic.

21. The apparatus of claim 20 wherein said means for controlling said voltage controlled oscillator includes means for monitoring the phase difference between a signal indicative of said voltage developed across said coil means and a signal indicative of said current through said coil means, means for providing a first phase indicative signal when said voltage signal leads said current signal in time and for providing a second phase indicative signal when said current signal leads said voltage signal in time, and further including means for controlling the control input of said voltage controlled oscillator in response to said first or second phase indicative signals so as to substantially eliminate the amount of phase difference between said voltage signal and said current signal of said coil.

22. A method for sensing a target characteristic and providing an electrical signal in response to said sensed target characteristic, said method comprising the steps of:

directing an electro-magnetic field at said target with a coil, said coil having an effective impedance value functionally related to said target characteristic;

energizing said coil at a resonant frequency functionally related to said target characteristic;

measuring said resonant frequency of said coil;

determining said impedance value of said coil when said frequency is at its resonant value;

determining said target characteristic in response to said measured frequency and said determined impedance value; and providing a target characteristic signal responsive to said determined target characteristic.

23. The method of claim 22 wherein said step of determining a target characteristic includes determining target material.

24. The method of claim 22 wherein said step of determining a target characteristic includes determining relative distance between said coil and said target.

25. The method of claim 22 wherein said step of determining a target characteristic includes determining target thickness.

26. The method of claim 22 wherein said target is made from at least two different materials and wherein said step of determining a target characteristic includes determining relative lateral position between said coil and said target.

27. The method of claim 22 further including the step of controlling a switch in response to said target characteristic signal.

28. The method of claim 22 further including the step of displaying information indicative of said target characteristic.

29. The method of claim 22 further including the step of controlling a mechanical actuator in response to said signal indicative of said target characteristic so as to control relative movement between said coil and said target in response to said target characteristic.

* * * * *